(12) United States Patent
Michihata (10) Patent No.: US 10,409,956 B2
(45) Date of Patent: Sep. 10, 2019

(54) MEDICAL SIGNAL PROCESSING APPARATUS AND MEDICAL OBSERVATION SYSTEM

(71) Applicant: Sony Olympus Medical Solutions Inc., Tokyo (JP)

(72) Inventor: Taihei Michihata, Kanagawa (JP)

(73) Assignee: Sony Olympus Medical Solutions Inc., Tokyo (JP)

( * ) Notice: Subject to any disclaimer, the term of this patent is extended or adjusted under 35 U.S.C. 154(b) by 265 days.

(21) Appl. No.: 15/418,928

(22) Filed: Jan. 30, 2017

(65) Prior Publication Data

US 2017/0270263 A1    Sep. 21, 2017

(30) Foreign Application Priority Data

Mar. 16, 2016  (JP) .................................. 2016-052989

(51) Int. Cl.
*G06F 11/30* (2006.01)
*G06F 19/00* (2018.01)

(52) U.S. Cl.
CPC ........ *G06F 19/3418* (2013.01); *G06F 19/321* (2013.01)

(58) Field of Classification Search
CPC .................................................. G06F 19/3418
See application file for complete search history.

(56) References Cited

FOREIGN PATENT DOCUMENTS

JP      2009-225851     * 10/2009

* cited by examiner

*Primary Examiner* — Phuong Huynh
(74) *Attorney, Agent, or Firm* — Oblon, McClelland, Maier & Neustadt, L.L.P.

(57) ABSTRACT

A medical signal processing apparatus receives input of an image signal corresponding to an inspection result of a subject and processes the image signal. The medical signal processing apparatus includes a programmable logic device including a plurality of functional blocks. Any functional block among the functional blocks is a communication functional block configured to communicate the image signal to another external device different from the medical signal processing apparatus. The communication functional block is individually resettable among the functional blocks.

10 Claims, 8 Drawing Sheets

MEDICAL SIGNAL PROCESSING APPARATUS AND MEDICAL OBSERVATION SYSTEM

CROSS-REFERENCE TO RELATED APPLICATION(S)

The present application claims priority to and incorporates by reference the entire contents of Japanese Patent Application No. 2016-052989 filed in Japan on Mar. 16, 2016.

BACKGROUND

The present disclosure relates to a medical signal processing apparatus and a medical observation system including the medical signal processing apparatus.

In the field of medicine, a medical observation system that images a subject such as the inside of a living body using an imaging element to observe the subject has been known (refer to Japanese Patent Application Laid-open No. 2009-225851, for example).

The medical observation system (an electronic endoscope system) described in Japanese Patent Application Laid-open No. 2009-225851 includes an electronic endoscope imaging the inside of a living body, a processor processing an imaging signal (an image signal) from the electronic endoscope, and a monitor displaying an image for observation based on a video signal processed by the processor.

The processor employs a field programmable gate array (FPGA) that reads configuration data stored in a read only memory (ROM) or the like in advance to construct a functional block (a logic circuit) that executes image processing.

In the medical observation system described in Japanese Patent Application Laid-open No. 2009-225851, when an abnormality occurs in image data processed by the functional block (when an abnormality occurs in the functional bock), the configuration data is read from the ROM again and the entire FPGA is reconstructed.

SUMMARY

The programmable logic device such as the FPGA may freely rewrite a functional block by configuration data and may thereby construct various functional blocks such as a communication functional block that communicates image signals to an external device in addition to the functional block performing the image processing. When such a communication functional block is constructed, when a communication error occurs in relation to the external device (when an abnormality occurs in the communication functional block), the image signal may not be communicated to the external device.

The medical observation system described in Japanese Patent Application Laid-open No. 2009-225851 reconstructs the entire FPGA when an abnormality occurs in the functional block, and the reconstruction takes time in accordance with the volume of the configuration data. In other words, a problem arises in that when a communication error occurs, it takes time to reconstruct the entire FPGA, and a state in which the image signal may be communicated may not be quickly restored.

There is a need for a medical signal processing apparatus and a medical observation system that quickly restore a state in which an image signal may be communicated even when a communication error occurs.

A medical signal processing apparatus according to one aspect of the present disclosure receives input of an image signal corresponding to an inspection result of a subject and processes the image signal. The medical signal processing apparatus includes: a programmable logic device including a plurality of functional blocks, any functional block among the functional blocks being a communication functional block configured to communicate the image signal to another external device different from the medical signal processing apparatus, wherein the communication functional block is individually resettable among the functional blocks.

DETAILED DESCRIPTION

The following describes an embodiment for performing the present disclosure (hereinafter, an embodiment) with reference to the accompanying drawings. The embodiment described below does not limit the present disclosure. Further, in the drawings, the same parts are denoted by the same symbols.

Schematic Configuration of Medical Observation System

Figure 1:
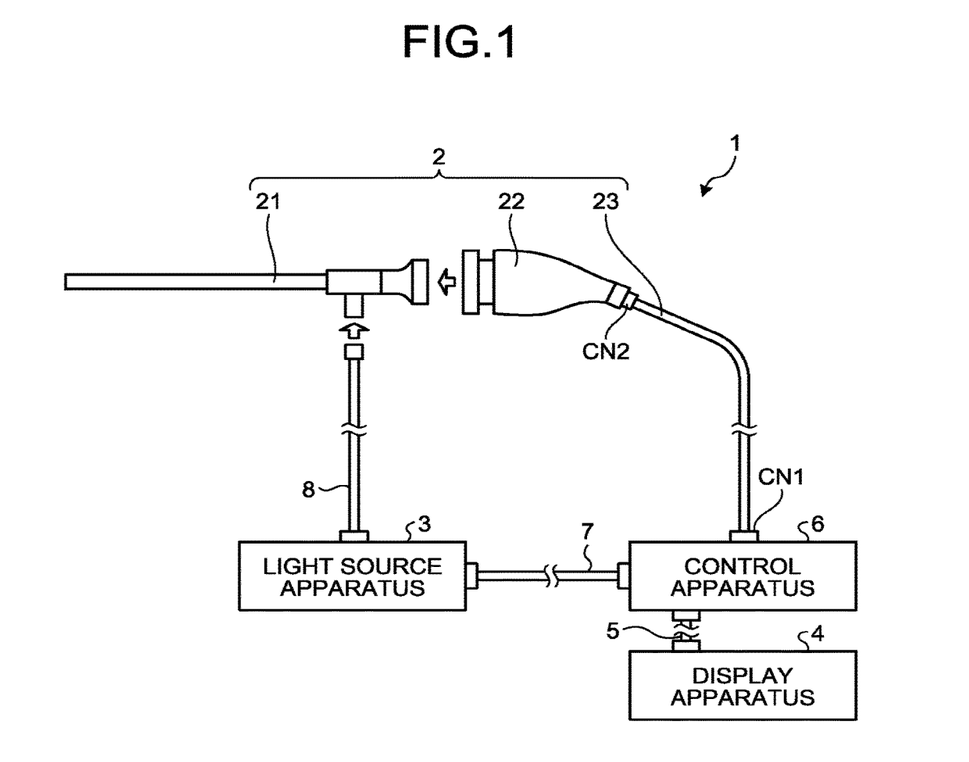
FIG. 1 is a diagram of a schematic configuration of a medical observation system according to an embodiment of the present disclosure.

FIG. 1 is a diagram of a schematic configuration of a medical observation system 1 according to the embodiment of the present disclosure.

The medical observation system 1 is used in the field of medicine and is a system for observing subjects such as the inside of a living body. As illustrated in FIG. 1, this medical observation system 1 includes an endoscope 2, a light source apparatus 3, a display apparatus 4, a second transmission cable 5, a control apparatus 6, a third transmission cable 7, and a light guide 8.

The endoscope 2 inspects the inside of a living body and outputs an image signal corresponding to the inspection result. As illustrated in FIG. 1, this endoscope 2 includes an inserting unit 21, a camera head 22, and a first transmission cable 23.

The inserting unit 21 is hard or at least partly soft, has an elongated shape, and is inserted into the inside of a living body. Within this inserting unit 21, an optical system including one or a plurality of lenses to collect a subject image is provided.

The light source apparatus 3, to which one end of the light guide 8 is connected, supplies light for illuminating the inside of a living body to the one end of the light guide 8 under the control of the control apparatus 6.

One end of the light guide 8 is detachably connected to the light source apparatus 3, whereas the other end thereof is detachably connected to the inserting unit 21. The light guide 8 transmits the light supplied from the light source apparatus 3 from the one end to the other end to supply the light to the inserting unit 21. The light supplied to the inserting unit 21 is emitted from the tip of the inserting unit 21 and is applied to the inside of a living body. The light applied to the inside of a living body (the subject image) is collected by the optical system within the inserting unit 21.

The camera head 22 is detachably connected to the basal end of the inserting unit 21. The camera head 22 images the subject image collected by the inserting unit 21 and outputs an imaging signal (an image signal) by the imaging under the control of the control apparatus 6.

A detailed configuration of the camera head 22 will be described below.

One end of the first transmission cable 23 is detachably connected to the control apparatus 6 via a connector CN1 (FIG. 1), whereas the other end thereof is connected to the camera head 22 via a connector CN2 (FIG. 1). The first transmission cable 23 transmits the image signal output from the camera head 22 to the control apparatus 6 and transmits a control signal, a synchronization signal, a clock, electric power, and the like output from the control apparatus 6 to the camera head 22.

As to the transmission of the image signal from the camera head 22 to the control apparatus 6 via the first transmission cable 23, the image signal may be transmitted through an optical signal or transmitted through an electric signal. The same holds true for the transmission of the control signal, the synchronization signal, and the clock from the control apparatus 6 to the camera head 22 via the first transmission cable 23.

The display apparatus 4 includes a display using liquid crystal, organic electro luminescence (EL), or the like and displays an image for observation based on a video signal processed by the control apparatus 6.

One end of the second transmission cable 5 is detachably connected to the display apparatus 4, whereas the other end thereof is detachably connected to the control apparatus 6. The second transmission cable 5 transmits the video signal processed by the control apparatus 6 to the display apparatus 4.

The control apparatus 6 includes a central processing unit (CPU) and comprehensively controls the operation of the light source apparatus 3, camera head 22, and the display apparatus 4.

A detailed configuration of the control apparatus 6 will be described below.

One end of the third transmission cable 7 is detachably connected to the light source apparatus 3, whereas the other end thereof is detachably connected to the control apparatus 6. The third transmission cable 7 transmits the control signal from the control apparatus 6 to the light source apparatus 3.

Configuration of Camera Head

The following describes the configuration of the camera head 22.

Figure 2:
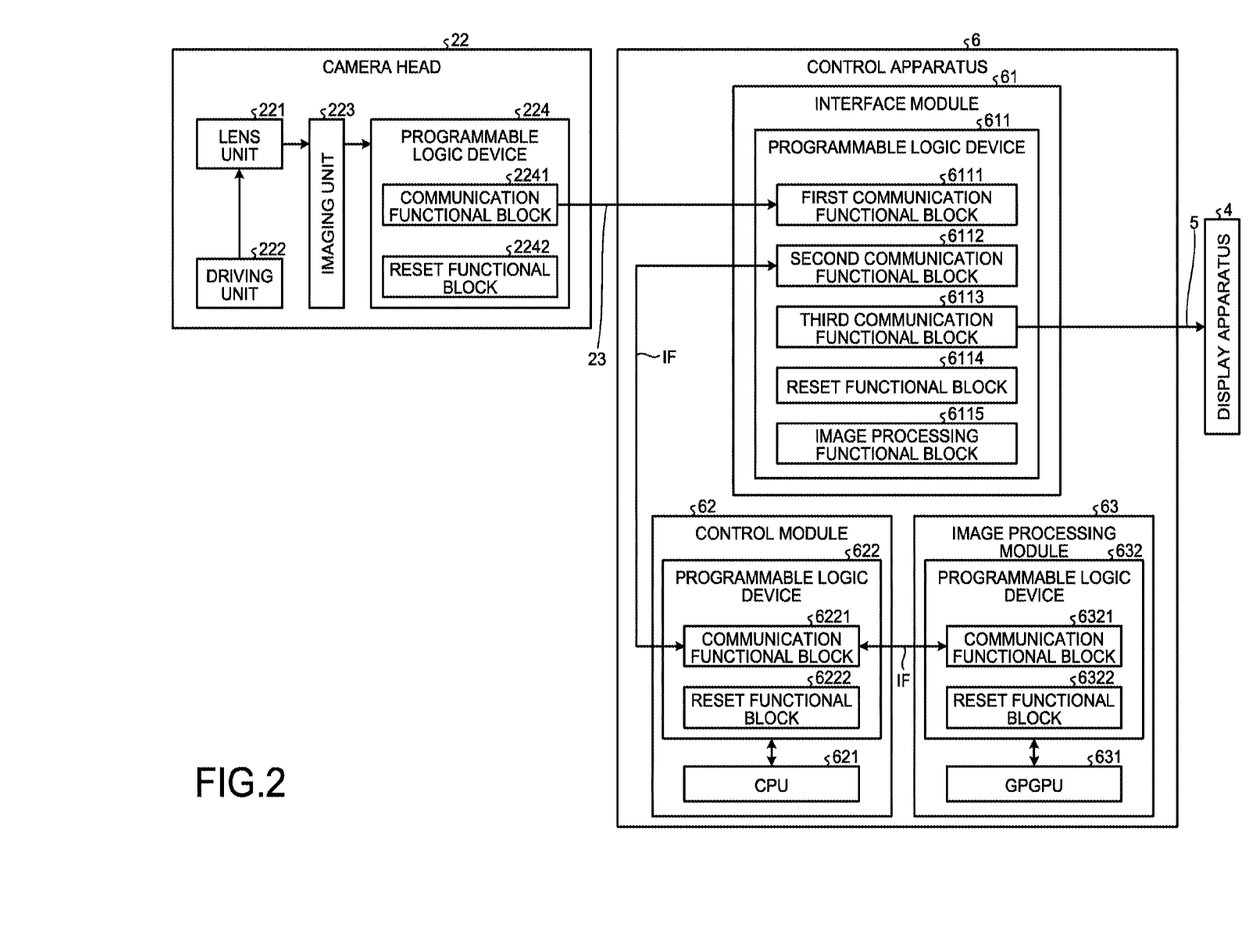
FIG. 2 is a block diagram of configurations of a camera head and a control apparatus illustrated in FIG. 1.

FIG. 2 is a block diagram of the configurations of the camera head 22 and the control apparatus 6.

FIG. 2 omits the illustration of the connectors CN1 and CN2 between the control apparatus 6 and the camera head 22 and the first transmission cable 23 and the connectors between the control apparatus 6 and the display apparatus 4 and the second transmission cable 5 for the convenience of description. As to the first transmission cable 23, FIG. 2 illustrates only a transmission path (electric wiring or an optical fiber) for the image signal from the camera head 22 to the control apparatus 6 and omits the illustration of a transmission path for the control signal, the synchronization signal, the clock, the electric power, and the like from the control apparatus 6 to the camera head 22.

As illustrated in FIG. 2, the camera head 22 includes a lens unit 221, a driving unit 222, an imaging unit 223, and a programmable logic device 224.

The lens unit 221 includes one or more lenses movable along an optical axis and forms the subject image collected by the inserting unit 21 onto the imaging plane of the imaging unit 223 (an imaging element (not illustrated)). The lens unit 221 includes an optical zooming mechanism (not illustrated) that moves the one or more lenses to change the angle of view and a focusing mechanism (not illustrated) that changes a focus.

The driving unit 222 actuates the optical zooming mechanism and the focusing mechanism under the control of the control apparatus 6 to change the angle of view or the focus of the lens unit 221.

The imaging unit 223 images the inside of a living body under the control of the control apparatus 6. This imaging unit 223 includes a sensor chip that integrally forms an imaging element (not illustrated) such as a charge coupled device (CCD) or a complementary metal oxide semiconductor (CMOS) that receives the subject image that has been collected by the inserting unit 21 and has been formed by the lens unit 221 to convert the subject image into an electric signal and a signal processing unit (not illustrated) that performs signal processing (A/D conversion and the like) on the electric signal (an analog signal) from the imaging element to output an image signal and outputs the image signal (a digital signal) after being subjected to the A/D conversion. The signal processing unit is not necessarily integrally formed with the imaging element and may be separate therefrom.

Figure 3:
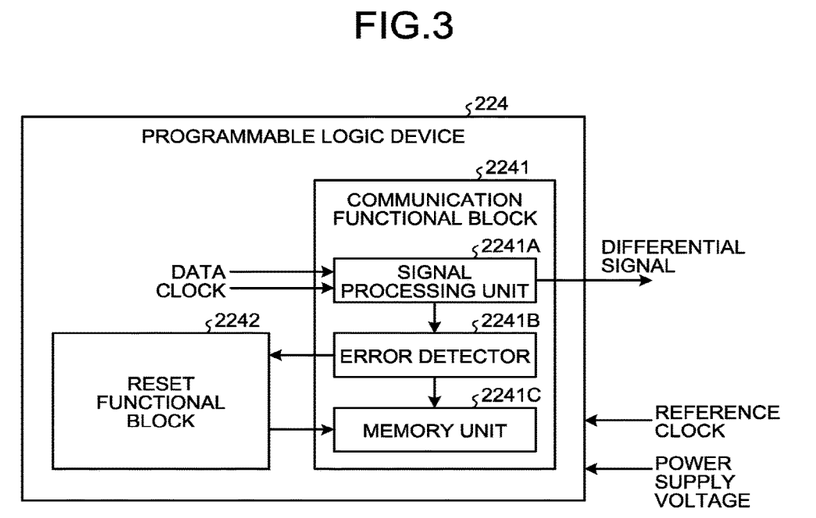
FIG. 3 is a block diagram of a configuration of a programmable logic device provided in the camera head illustrated in FIG. 2.

FIG. 3 is a block diagram of a configuration of the programmable logic device 224 provided in the camera head 22.

The programmable logic device 224 has functions as the medical signal processing apparatus according to the present disclosure. In the present embodiment, the programmable logic device 224 includes an FPGA that constructs a plurality of functional blocks (logic circuits) by reading configuration data recorded in a non-volatile memory (not illustrated) such as an electrically erasable programmable read-only memory (EEPROM) in advance. As illustrated in FIG. 2 or FIG. 3, this programmable logic device 224 includes a communication functional block 2241 and a reset functional block 2242.

The programmable logic device 224 may include, other than the communication functional block 2241 and the reset functional block 2242, any functional block that executes processing different from those by the functional blocks 2241 and 2242. The following describes only the functions of the communication functional block 2241 and the reset functional block 2242, which are principal parts of the present disclosure, as the programmable logic device 224. FIG. 2 and FIG. 3 illustrate only the functional blocks 2241 and 2242.

The communication functional block 2241 functions as a transmitter that transmits the image signal from the imaging unit 223 to the control apparatus 6 via the first transmission cable 23. In the present embodiment, the communication functional block 2241 includes a high speed serial interface that communicates the image signal at a transmission rate of 1 Gbps or more to the control apparatus 6 via the first transmission cable 23. As illustrated in FIG. 3, this communication functional block 2241 includes a signal processing unit 2241A, an error detector 2241B, and a memory unit 2241C.

The signal processing unit 2241A is a part that executes transmission processing for transmitting the image signal to the control apparatus 6 and includes an encoder, a phase locked loop (PLL), a FIFO, and a differentiating unit, although their specific illustration is omitted. The encoder performs encoding processing (N-bit/M(>N)-bit conversion processing (8-bit/10-bit conversion processing, for example)) to generate a signal in which a clock is superimposed on the data (the image signal) from the imaging unit 223. The FIFO performs clock changing processing on the signal generated by the encoder using a clock generated by the PLL based on a reference clock input from the control apparatus 6 via the first transmission cable 23. The differentiating unit generates a differential signal from the signal on which the clock changing processing has been performed by the FIFO and outputs the differential signal (an image signal) to the control apparatus 6 via the first transmission cable 23. FIG. 3 illustrates two differential signal lines by one signal line for the convenience of description (the same holds true for FIG. 4).

The error detector 2241B detects an abnormal state in the signal processing unit 2241A. Specifically, the error detector 2241B detects abnormal states such as a state in which the PLL is not in a locked state, a state in which a clock changing error is occurring in the FIFO, and a state in which the differential signal may not be generated by the differentiating unit in the signal processing unit 2241A. When detecting any abnormal state in the signal processing unit 2241A, the error detector 2241B outputs an error signal to the reset functional block 2242 and the memory unit 2241C.

In response to the error signal from the error detector 2241B, the memory unit 2241C stores therein abnormality information indicating the abnormality in the signal processing unit 2241A.

The reset functional block 2242 is a part that attempts return of the signal processing unit 2241A (shift from the abnormal state to a normal state) in response to the error signal from the error detector 2241B. Specifically, when the memory unit 2241C once stores therein the abnormality information, the signal processing unit 2241A continues the abnormal state and does not operate normally. Given this situation, the reset functional block 2242 initializes the memory unit 2241C (erases the abnormality information) in response to the error signal from the error detector 2241B to attempt the return of the signal processing unit 2241A. In other words, in the present embodiment, when an abnormality occurs (when a communication error occurs) in the communication functional block 2241 (the signal processing unit 2241A), the memory unit 2241C is initialized to reset only the communication functional block 2241 without reconstructing the entire programmable logic device 224.

An abnormality in the signal processing unit 2241A is likely to occur immediately after the startup (immediately after the power-on) of the medical observation system 1. Specifically, immediately after the startup of the medical observation system 1, the reference clock and the power supply voltage input to the programmable logic device 224 are unstable. When there is no clock oscillator and power supply in the camera head 22, for example, the control apparatus 6 supplies the reference clock and the power supply voltage to the programmable logic device 224 via the first transmission cable 23. For this reason, with loss (deterioration of signal quality and the like) or delay during transmission added, the reference clock and the power supply voltage input to the programmable logic device 224 are unstable during the startup.

Given these circumstances, the reset functional block 2242 initializes the memory unit 2241C (resets the communication functional block 2241) only when an error signal is output from the error detector 2241B for a certain period after the startup of the medical observation system 1 (for a prescribed time until the display apparatus 4 displays the image for observation after the startup of the medical observation system 1).

Configuration of Control Apparatus

The following describes the configuration of the control apparatus 6 with reference to FIG. 2.

The control apparatus 6 is assembled using general-purpose PC architecture. Specifically, as illustrated in FIG. 2, the control apparatus 6 has a configuration that connects an interface module 61, a control module 62, and an image processing module 63 using general-purpose interfaces IF.

The interface IF is an interface at least, out of a communication protocol and a connector shape, the communication protocol or both of which is compliant with a communication interface standard (the PC/AT compatible standard, for example).

The present embodiment employs PCI Express (PCIe) (registered trademark) or the like for the interface IF. In the present embodiment, the control module 62 and the image processing module 63 out of the three modules 61 to 63 each include what is called PC parts compliant with the PCIe standard. In other words, the interface module 61 has a connecting part other than the interface IF. However, the interface module 61 may also include what is called PC parts similarly to the control module 62 and the image processing module 63.

The control module 62 controls the operation of the light source apparatus 3, the operation of the camera head 22, the operation of the display apparatus 4, and the operation of the entire control apparatus 6.

In the present embodiment, the control module 62 includes a mother board compliant with the PC/AT compatible standard on which a CPU 621 (FIG. 2), a programmable logic device 622 (FIG. 2), and the like are mounted. The mother board includes expansion slots (PCIe slots in the present embodiment) each for connecting the interface module 61 and the image processing module 63.

At least any of the interfaces IF among the modules 61 to 63 may have an original connector shape, for example, not a connector shape compliant with the communication interface standard, and further, may be an interface IF that provides direct connection with electric wiring or the like without having connectors and is compliant with the communication protocol of the communication interface standard.

A detailed configuration of the programmable logic device 622 will be described below.

The interface module 61 is mounted on the expansion slot (the PCIe slot in the present embodiment) provided in the control module 62. This interface module 61 includes a programmable logic device 611 (FIG. 2) including an FPGA similarly to the programmable logic device 224 provided in the camera head 22.

Figure 4:
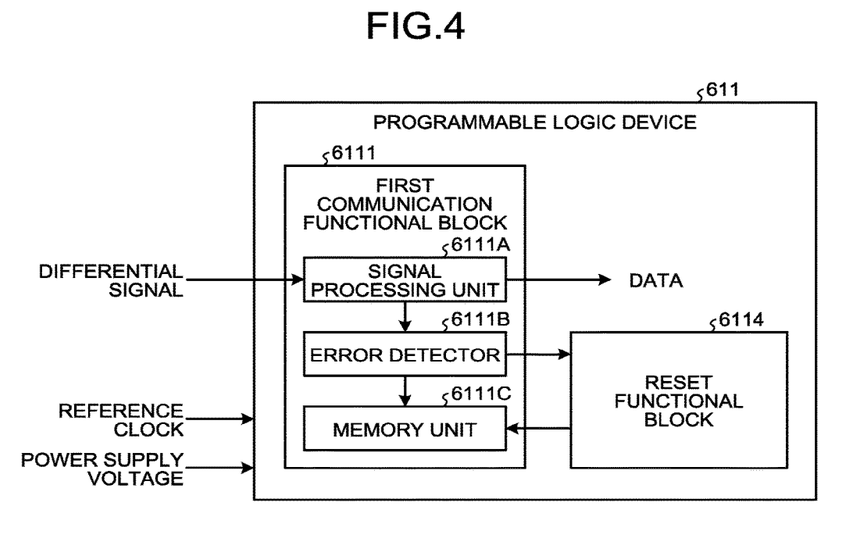
FIG. 4 is a block diagram of a configuration of a programmable logic device provided in an interface module illustrated in FIG. 2.

FIG. 4 is a diagram of a configuration of the programmable logic device 611 provided in the interface module 61.

The programmable logic device 611 has functions as the medical signal processing apparatus according to the present disclosure. As illustrated in FIG. 2, this programmable logic device 611 includes a first communication functional block 6111, a second communication functional block 6112, a third communication functional block 6113, a reset functional block 6114, and an image processing functional block 6115.

The programmable logic device 611 may include, other than the functional blocks 6111 to 6115, any functional block that executes processing different from those by the functional blocks 6111 to 6115. The following describes only the functions of the functional blocks 6111 to 6115, which are principal parts of the present disclosure, as the programmable logic device 611. FIG. 4 illustrates only the first communication functional block 6111 and the reset functional block 6114 among the functional blocks of the programmable logic device 611 f for the convenience of description.

The first communication functional block 6111 functions as a receiver that receives the image signal (the differential signal) from the camera head 22 (the communication functional block 2241) via the first transmission cable 23. In the present embodiment, the first communication functional block 6111 includes, corresponding to the communication functional block 2241, a high speed serial interface that communicates the image signal at a transmission rate of 1 Gbps or more to the communication functional block 2241. As illustrated in FIG. 4, this first communication functional block 6111 includes a signal processing unit 6111A, an error detector 6111B, and a memory unit 6111C.

The signal processing unit 6111A is a part that executes reception processing for receiving the image signal from the camera head 22 and includes a singulating unit, a PLL, a clock recovery (CDR), a decoder, and a FIFO, although their specific illustration is omitted. The singulating unit singulates the image signal (the differential signal) from the communication functional block 2241. The CDR reproduces a superimposed clock from the image signal singulated by the singulating unit using a clock generated by the PLL based on a reference clock input from the outside of the programmable logic device 611. The decoder performs decoding processing (M-bit/N(<M)-bit conversion processing (10-bit/8-bit conversion processing, for example)) on the image signal singulated by the singulating unit. The FIFO performs clock changing processing on the image signal on which the decoding processing has been executed by the decoder. The signal processing unit 6111A outputs an image signal (data) on which the clock changing processing has been executed. The image signal output from the signal processing unit 6111A is once stored in a memory (not illustrated) such as a video RAM (VRAM) provided outside the programmable logic device 611 (within the interface module 61).

The error detector 6111B detects an abnormal state in the signal processing unit 6111A. Specifically, the error detector 6111B detects abnormal states such as a state in which the clock may not be generated by the CDR, a state in which the PLL is not in a locked state, a state in which a clock changing error is occurring in the FIFO in the signal processing unit 6111A. When detecting any abnormal state in the signal processing unit 6111A, the error detector 6111B outputs an error signal to the reset functional block 6114 and the memory unit 6111C.

In response to the error signal from the error detector 6111B, the memory unit 6111C stores therein abnormality information indicating the abnormality in the signal processing unit 6111A.

The second communication functional block 6112 communicates with the control module 62 via the interface IF (PCIe in the present embodiment). This second communication functional block 6112 integrally includes a transmitter having a configuration (a signal processing unit performing transmission processing, an error detector detecting an abnormal state in the signal processing unit, and a memory unit that stores therein abnormality information indicating the abnormality in the signal processing unit) substantially similar to that of the communication functional block 2241 provided in the camera head 22 and a receiver having a configuration (a signal processing unit performing reception processing, an error detector detecting an abnormal state in the signal processing unit, and a memory unit that stores therein abnormality information indicating the abnormality in the signal processing unit) substantially similar to that of the first communication functional block 6111, although their specific illustration is omitted.

The second communication functional block 6112 transmits the image signal that has been output from the first communication functional block 6111 and has been once stored in the memory (not illustrated) such as the VRAM to the control module 62 via the interface IF. The second communication functional block 6112 receives a first video signal generated by the image processing module 63 from the control module 62 via the interface IF.

The image processing functional block 6115 performs various kinds of image processing (image processing simpler (the processing load of which is lighter) than the image processing by the image processing module 63) on the image signal that has been output from the first communication functional block 6111 and has been once stored in the memory (not illustrated) such as the VRAM in place of the image processing module 63 when a malfunction occurs in the image processing module 63, for example, to generate a second video signal.

The third communication functional block 6113 functions as a transmitter having a configuration (a signal processing unit performing transmission processing, an error detector detecting an abnormal state in the signal processing unit, and a memory unit that stores therein abnormality information indicating the abnormality in the signal processing unit) substantially similar to that of the communication functional block 2241 provided in the camera head 22, although their specific illustration is omitted. The third communication functional block 6113 transmits the first video signal received by the second communication functional block 6112 or the second video signal generated by the image processing functional block 6115 to the display apparatus 4 via the second transmission cable 5. Upon reception of the first video signal or the second video signal, the display apparatus 4 displays a regular image (an image for observation) based on the first video signal or a simple image (an image for observation) based on the second video signal.

In the present embodiment, the third communication functional block 6113 includes a high speed serial interface that communicates the image signal at a transmission rate of 1 Gbps or more to the display apparatus 4 via the second transmission cable 5.

The reset functional block 6114 has a function similar to that of the reset functional block 2242 provided in the camera head 22. In other words, when an error signal is output from the first communication functional block 6111 (the error detector 6111B), the reset functional block 6114 initializes the memory unit 6111C to reset only the first communication functional block 6111 without reconstructing the entire programmable logic device 611. Also when an error signal is output from the second and third communication functional blocks 6112 and 6113, the reset functional block 6114 similarly initializes the memory unit included in the communication functional block that has output the error signal to rest only the communication functional block. The reset by the reset functional block 6114 is executed only for a certain period after the startup of the medical observation system 1 (a prescribed time until the display apparatus 4 displays the image for observation after the startup of the medical observation system 1) similarly to that by the reset functional block 2242.

The programmable logic device 622 included in the control module 62 has functions as the medical signal processing apparatus according to the present disclosure and includes an FPGA similarly to the programmable logic device 224 provided in the camera head 22 and the programmable logic device 611 provided in the interface module 61. As illustrated in FIG. 2, this programmable logic device 622 includes a communication functional block 6221 and a reset functional block 6222.

The programmable logic device 622 may include, other than the functional blocks 6221 and 6222, any functional block that executes processing different from those by the communication functional blocks 6221 and 6222. The following describes only the functions of the functional blocks 6221 and 6222, which are principal parts of the present disclosure, as the programmable logic device 622. FIG. 2 illustrates only the functional blocks 6221 and 6222.

The communication functional block 6221 communicates with the interface module 61 via the interface IF (PCIe in the present embodiment). This communication functional block 6221 has a configuration (a configuration that integrates a transmitter and a receiver) similar to that of the second communication functional block 6112 provided in the interface module 61, although its specific illustration is omitted.

The communication functional block 6221 transmits the image signal received from the interface module 61 (the second communication functional block 6112) via the interface IF to the image processing module 63 via the interface IF. The communication functional block 6221 transmits the first video signal received from the image processing module 63 via the interface IF to the interface module 61 (the second communication functional block 6112) via the interface IF.

The reset functional block 6222 has a function similar to those of the reset functional block 2242 provided in the camera head 22 and the reset functional block 6114 provided in the interface module 61. In other words, when an error signal is output from the communication functional block 6221, the reset functional block 6222 initializes the memory unit (not illustrated) included in the communication functional block 6221 to reset only the communication functional block 6221 without reconstructing the entire programmable logic device 622. The reset by the reset functional block 6222 is executed only for a certain period after the startup of the medical observation system 1 (a prescribed time until the display apparatus 4 displays the image for observation after the startup of the medical observation system 1) similarly to that by the reset functional blocks 2242 and 6114.

The image processing module 63 is a module on which a general-purpose computing on graphics processing unit (GPGPU) 631 (FIG. 2) and a programmable logic device 632 (FIG. 3) are mounted and is mounted on the expansion slot (the PCIe slot in the present embodiment) provided in the control module 62.

The programmable logic device 632 has functions as the medical signal processing apparatus according to the present disclosure and includes an FPGA similarly to the programmable logic device 224 provided in the camera head 22, the programmable logic device 611 provided in the interface module 61, and the programmable logic device 622 provided in the control module 62. As illustrated in FIG. 2, this programmable logic device 632 includes a communication functional block 6321 and a reset functional block 6322.

The programmable logic device 632 may include, other than the functional blocks 6321 and 6322, any functional block that executes processing different from those by the communication functional blocks 6321 and 6322. The following describes only the functions of the functional blocks 6321 and 6322, which are principal parts of the present disclosure, as the programmable logic device 632. FIG. 2 illustrates only the functional blocks 6321 and 6322.

The communication functional block 6321 communicates with the control module 62 via the interface IF (PCIe in the present embodiment). This communication functional block 6321 has a configuration (a configuration that integrates a transmitter and a receiver) similar to that of the communication functional block 6221 provided in the control module 62, although its specific illustration is omitted.

The communication functional block 6321 outputs the image signal received from the control module 62 (the communication functional block 6221) via the interface IF to the GPGPU 631. The communication functional block 6321 transmits the first video signal generated by the communication functional block 6321 to the control module (the communication functional block 6221) via the interface IF.

The reset functional block 6322 has a function similar to those of the reset functional block 2242 provided in the camera head 22, the reset functional block 6114 provided in the interface module 61, and the reset functional block 6222 provided in the control module 62. In other words, when an error signal is output from the communication functional block 6321, the reset functional block 6322 initializes the memory unit (not illustrated) included in the communication functional block 6321 to reset only the communication functional block 6321 without reconstructing the entire programmable logic device 632. The reset by the reset functional block 6322 is executed only for a certain period after the startup of the medical observation system 1 (a prescribed time until the display apparatus 4 displays the image for observation after the startup of the medical observation system 1) similarly to those by the reset functional blocks 2242, 6114, and 6222.

The GPGPU 631 performs various kinds of processing such as development processing, noise reduction, color correction, color enhancement, and edge enhancement on the image signal received from the control module 62 by the programmable logic device 632 (the communication functional block 6321) to generate the first video signal.

Operation of Programmable Logic Device

The following describes operations of the programmable logic devices 224, 611, 622, and 632. The operations of the programmable logic devices 224, 611, 622, and 632 are substantially the same, and the following describes the operation of the programmable logic device 224.

Figure 5:
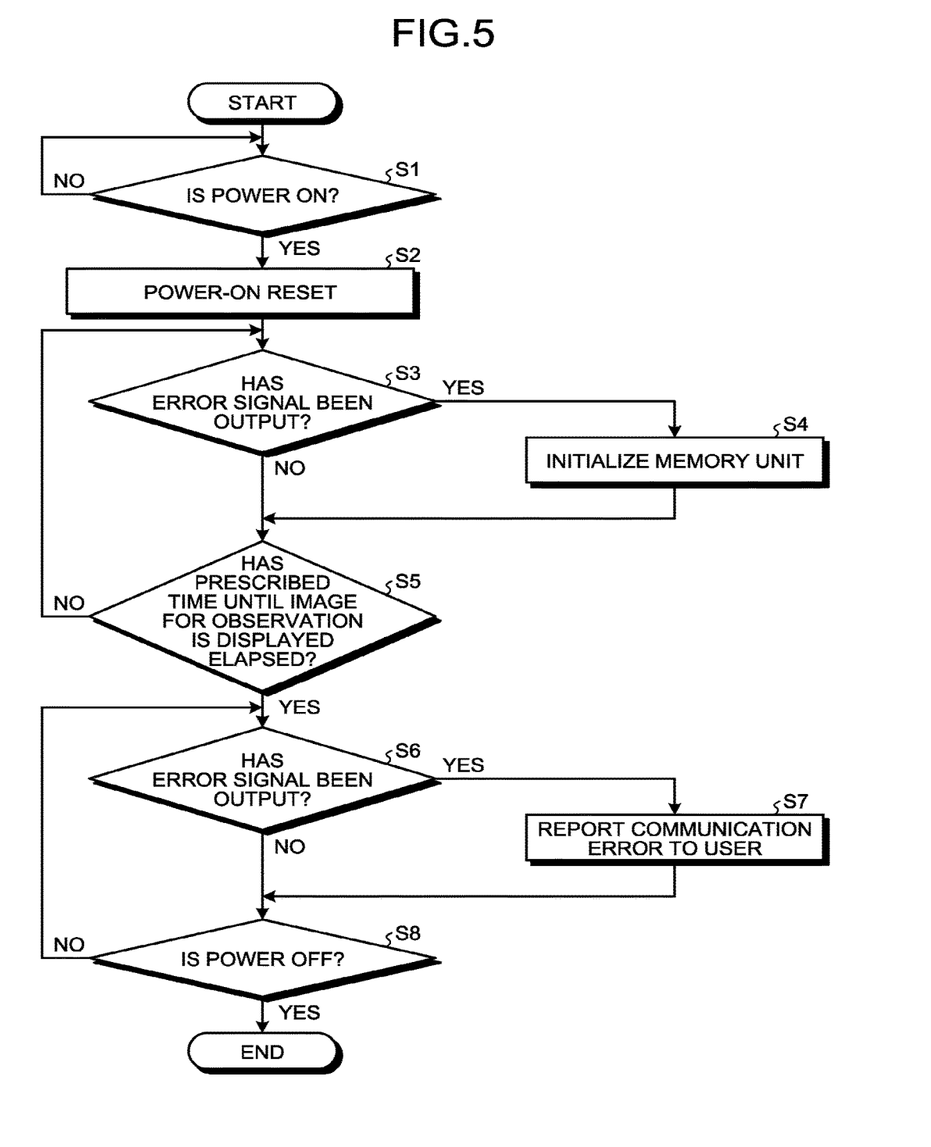
FIG. 5 is a flowchart of operation of the programmable logic device illustrated in FIG. 3.

FIG. 5 is a flowchart of the operation of the programmable logic device 224.

When the medical observation system 1 starts up (Yes at Step S1), and electric power is supplied from the control apparatus 6 to the camera head 22, the programmable logic device 224 executes power-on reset (Step S2). In other words, configuration data recorded in a non-volatile memory (not illustrated) such as an EEPROM in advance is read, whereby the communication functional block 2241 and the reset functional block 2242 are constructed.

After Step S2, the reset functional block 2242 determines whether an error signal has been output from the error detector 2241B (Step S3).

If it is determined that an error signal has been output (Yes at Step S3), abnormality information is stored in the memory unit 2241C in response to the error signal, and the reset functional block 2242 initializes the memory unit 2241C (erases the abnormality information) (Step S4).

If it is determined that no error signal has been output (No at Step S3) or after Step S4, the reset functional block 2242 determines whether a prescribed time has elapsed until the display apparatus 4 displays the image for observation after the startup of the medical observation system 1 (Step S5).

If it is determined that the prescribed time has not elapsed (No at Step S5), the reset functional block 2242 returns to Step S3.

In contrast, if it is determined that the prescribed time has elapsed (Yes at Step S5), the reset functional block 2242 determines whether an error signal has been output from the error detector 2241B similarly to Step S3 (Step S6).

If it is determined that an error signal has been output (Yes at Step S6), the programmable logic device 224 actuates a light emitting diode (LED), a speaker, a display unit, or the like (not illustrated) provided in the camera head 22 to report the fact that a communication error is occurring to a user such as an operator (Step S7).

If it is determined that no error signal has been output (No at Step S6) or after Step S7, the programmable logic device 224 repeatedly executes Steps S6 and S7 until the power is off (Yes at Step S8).

The programmable logic device 224 according to the present embodiment described above may individually reset the communication functional block 2241 among the functional blocks without reconstructing the entire programmable logic device 224. In other words, even when a communication error occurs (when an abnormality occurs in the communication functional block 2241), only the communication functional block 2241 among the functional blocks is reset to restore a state in which the image signal may be communicated. This holds true for the other programmable logic devices 611, 622, and 632.

Consequently, the programmable logic devices 224, 611, 622, and 632 according to the present embodiment produce an effect of making it possible to restore a state in which the image signal may be communicated quickly even when a communication error occurs compared with a conventional configuration in which when an abnormality occurs in the functional block, the entire FPGA is reconstructed.

In the programmable logic device 224 according to the present embodiment, the reset of the communication functional block 2241 is executed by the initialization of the memory unit 2241C (the erasure of the abnormality information).

Consequently, the communication functional block 2241 may be individually reset easily and quickly. This holds true for the other programmable logic devices 611, 622, and 632.

In particular, the communication functional block 2241 includes the memory unit 2241C.

Consequently, the configuration of the programmable logic device 224 is less complicated than a configuration (refer to FIG. 6A) in which the memory unit 2241C is included in the programmable logic device 224 as a functional block similarly to the communication functional block 2241 and the reset functional block 2242, for example. This holds true for the other programmable logic devices 611, 622, and 632.

In the programmable logic device 224 according to the present embodiment, the communication functional block 2241 includes the error detector 2241B that performs self-diagnosis (detection of an abnormal state in the signal processing unit 2241A). The reset functional block 2242 resets the communication functional block 2241 in response to the error signal from the error detector 2241B. This holds true for the other programmable logic devices 611, 622, and 632.

Consequently, the configurations of the programmable logic devices 224, 611, 622, and 632 may be simplified, and thus, the structure of the entire medical observation system 1 may be simplified compared with a configuration in which other functional blocks other than the communication functional blocks 2241, 6111 to 6113, 6221, and 6321 and external devices different from the programmable logic devices 224, 611, 622, and 632 are caused to detect the abnormal state of the communication functional blocks 2241, 6111 to 6113, 6221, and 6321.

As described above, the abnormality in the communication functional blocks 2241, 6111 to 6113, 6221, and 6321 is likely to occur in a state in which the reference clock and the power supply voltage are unstable immediately after the startup of the medical observation system 1. When the communication functional blocks 2241, 6111 to 6113, 6221, and 6321 include a high speed serial interface that communicates a signal in which a clock is superimposed on an image signal at a transmission rate of 1 Gbps or more in particular, the communication functional blocks 2241, 6111 to 6113, 6221, and 6321 are likely to be significantly influenced by the state in which the reference clock and the power supply voltage are unstable (are likely to become an abnormal state).

In the programmable logic devices 224, 611, 622, and 632 according to the present embodiment, only immediately after the startup of the medical observation system 1 (a prescribed time until the display apparatus 4 displays the image for observation after the startup of the medical observation system 1), only the communication functional blocks 2241, 6111 to 6113, 6221, and 6321 may be reset.

Consequently, even for a configuration that is likely to cause a communication error immediately after the startup of the medical observation system 1, a configuration that restores a state in which the image signal may be communicated quickly and efficiently may be achieved.

Other Embodiments

Although the embodiment for performing the present disclosure has been described, the present disclosure should not be limited to the embodiment alone.

Figure 6A:
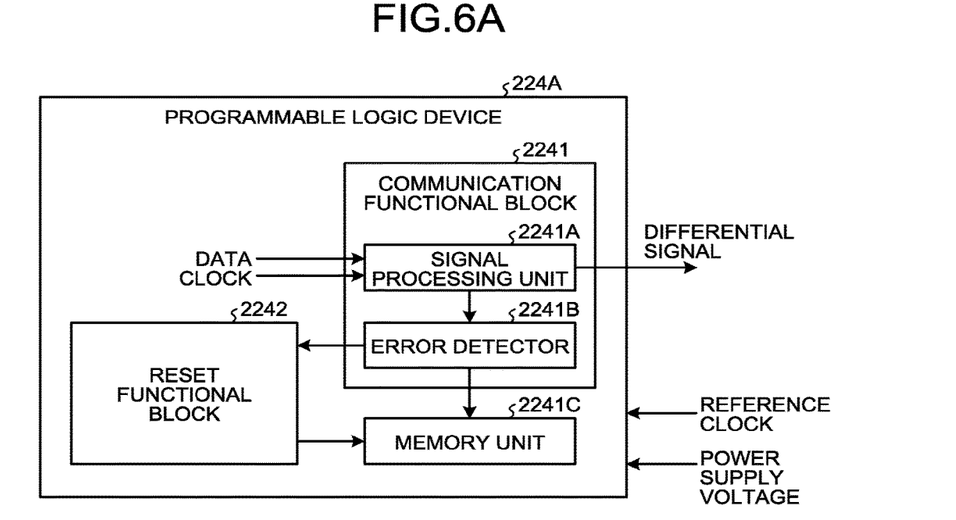
FIG. 6A is a diagram of a modification of the embodiment of the present disclosure, which is a diagram illustrating a configuration of a programmable logic device according to the modification.
Figure 6B:
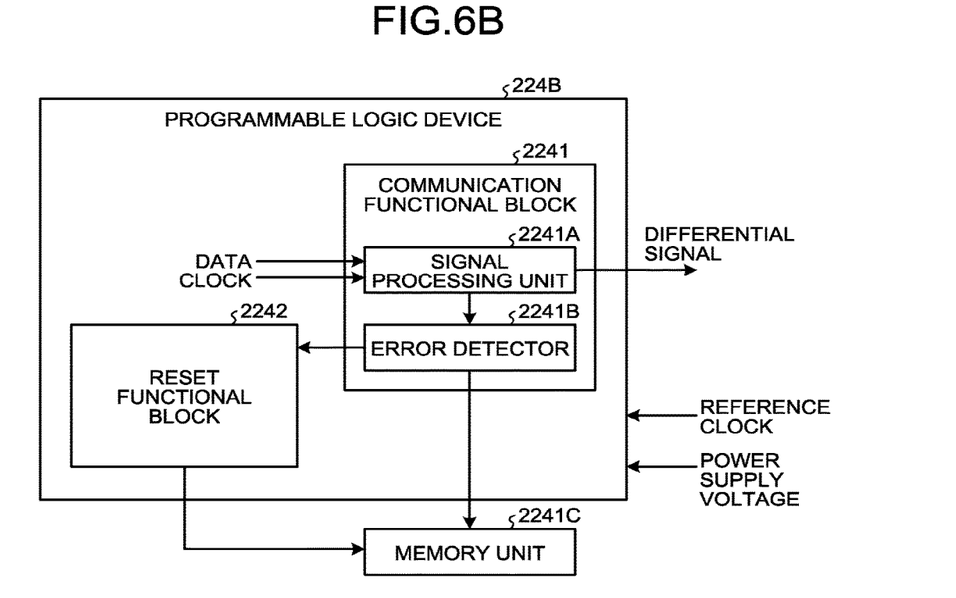
FIG. 6B is a diagram of a modification of the embodiment of the present disclosure, which is a diagram illustrating a configuration of a programmable logic device according to the modification.

FIG. 6A and FIG. 6B are diagrams of modifications of an embodiment of the present disclosure, which are block diagrams of configurations of programmable logic devices 224A and 224B according to the modifications.

Although the memory unit 2241C is provided within the communication functional block 2241 in the programmable logic device 224 provided in the camera head 22 in the embodiment, this is not limiting.

As illustrated in FIG. 6A, the memory unit 2241C may be included in the programmable logic device 224A as a functional block separate from the communication functional block 2241, for example. As illustrated in FIG. 6B, the memory unit 2241C may be provided outside the programmable logic device 224B (within the camera head 22), for example.

Although FIG. 6A and FIG. 6B illustrate the modifications of the programmable logic device 224 provided in the camera head 22 for the convenience of description, also in the programmable logic device 611 provided in the interface module 61, the programmable logic device 622 provided in the control module 62, and the programmable logic device 632 provided in the image processing module 63, the memory unit (not illustrated) that stores therein the abnormality information of the signal processing unit (not illustrated) included in the communication functional blocks 6111 to 6113, 6221, and 6321 may be similarly provided similarly to FIG. 6A and FIG. 6B.

Figure 7:
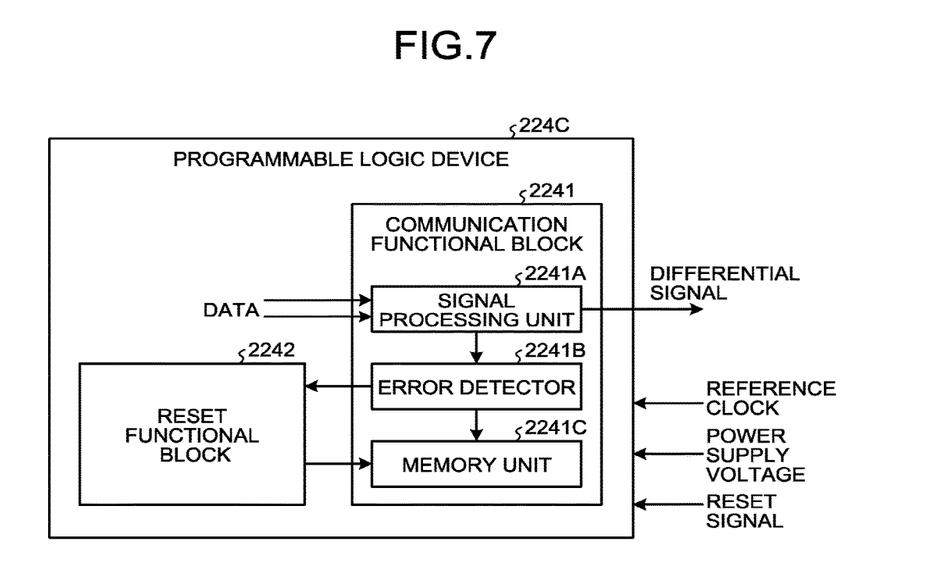
FIG. 7 is a diagram of a modification of the embodiment of the present disclosure, which is a diagram illustrating a configuration of a programmable logic device according to the modification.

FIG. 7 is a diagram of a modification of an embodiment of the present disclosure, which is a block diagram of a configuration of a programmable logic device 224C according to the modification.

Although the reset functional block 2242 initializes the memory unit 2241C (rests the communication functional block 2241) in response to the error signal from the error detector 2241B in the programmable logic device 224 provided in the camera head 22 in the embodiment, this is not limiting.

As illustrated in FIG. 7, the reset functional block 2242 may be configured to initialize the memory unit 2241C in response to a reset signal input from the outside of the programmable logic device 224C, for example. Examples of a configuration that outputs the reset signal include a programmable logic device as the other party of communication (the programmable logic device 611 provided in the interface module 61 in FIG. 7).

Although FIG. 7 illustrates the modification of the programmable logic device 224 provided in the camera head 22 for the convenience of description, also in the programmable logic device 611 provided in the interface module 61, the programmable logic device 622 provided in the control module 62, and the programmable logic device 632 provided in the image processing module 63, the reset functional blocks 6114, 6222, and 6322 may be similarly configured to initialize the memory unit (not illustrated) (reset the communication functional blocks 6111 to 6113, 6221, and 6321) in response to the reset signal.

When the programmable logic devices are configured as described above, communication errors that may not be detected by the self-diagnosis of the communication functional blocks 2241, 6111 to 6113, 6221, and 6321 are detected by other devices, and the abnormal state of the communication functional blocks 2241, 6111 to 6113, 6221, and 6321 may be appropriately returned to the normal state.

Figure 8:
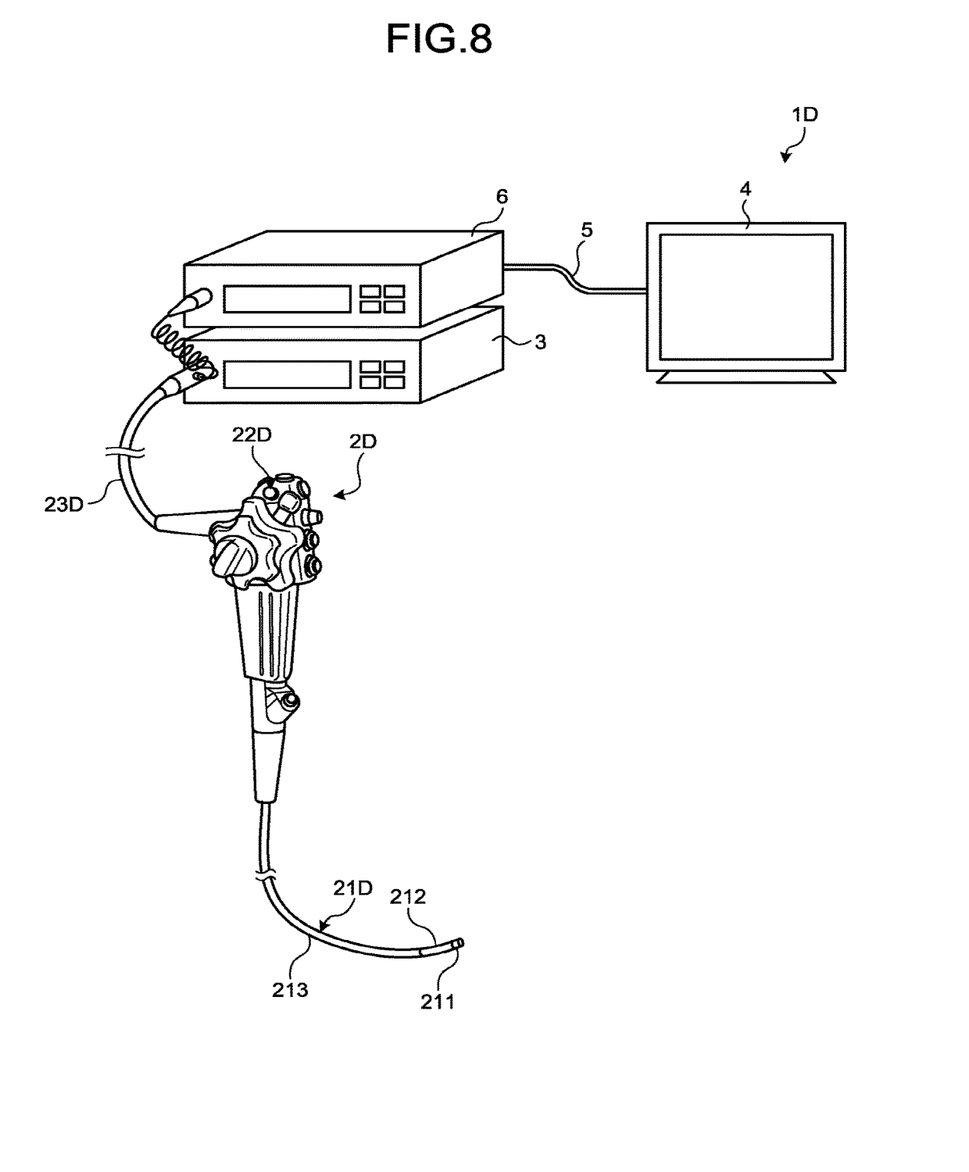
FIG. 8 is a diagram of a modification of the embodiment of the present disclosure, which is a diagram illustrating a schematic configuration of a medical observation system according to the present modification.

FIG. 8 is a diagram of a modification of an embodiment of the present disclosure, which is a diagram of a schematic configuration of a medical observation system 1D according to the modification.

Although the present disclosure is applied to the endoscope 2 including the camera head 22 in the medical observation system 1 according to the embodiment, this is not limiting; the present disclosure may be applied to what is called a video scope having an imaging unit on the tip side of an inserting unit of an endoscope as in the medical observation system 1D illustrated in FIG. 8.

The medical observation system 1D according to the present modification includes an endoscope 2D that inserts an inserting unit 21D into the inside of a living body to take an internal image of an observation site and to generate an image signal, the light source apparatus 3 that generates illumination light to be emitted from the tip of the endoscope 2D, the control apparatus 6 that processes the image signal generated by the endoscope 2D, and the display apparatus 4 that is connected to the control apparatus 6 via the second transmission cable 5 to display an image for observation based on a video signal processed by the control apparatus 6.

As illustrated in FIG. 8, the endoscope 2D includes the inserting unit 21D having an elongated shape with flexibility, an operating unit 22D that is connected to the basal end of the inserting unit 21D and receives input of various kinds of operational signals, and a universal cord 23D that extends from the operating unit 22D in a direction different from the direction in which the inserting unit 21D extends and incorporates various kinds of cables that connect the light source apparatus 3 and the control apparatus 6.

The inserting unit 21D includes a tip part 211 incorporating an imaging unit (not illustrated) that images the inside of a living body to generate an image signal, a bendable bent part 212 formed of a plurality of bending pieces, and a flexible, elongated flexible tube part 213 that is connected to the basal end of the bent part 212.

The operating unit 22D incorporates a configuration similar to that of the programmable logic device 224 described in the embodiment, although its specific illustration is omitted, and the image signal generated by the imaging unit is processed by the programmable logic device. The programmable logic device transmits the processed image signal to the control apparatus 6 via the universal cord 23D.

Figure 9:
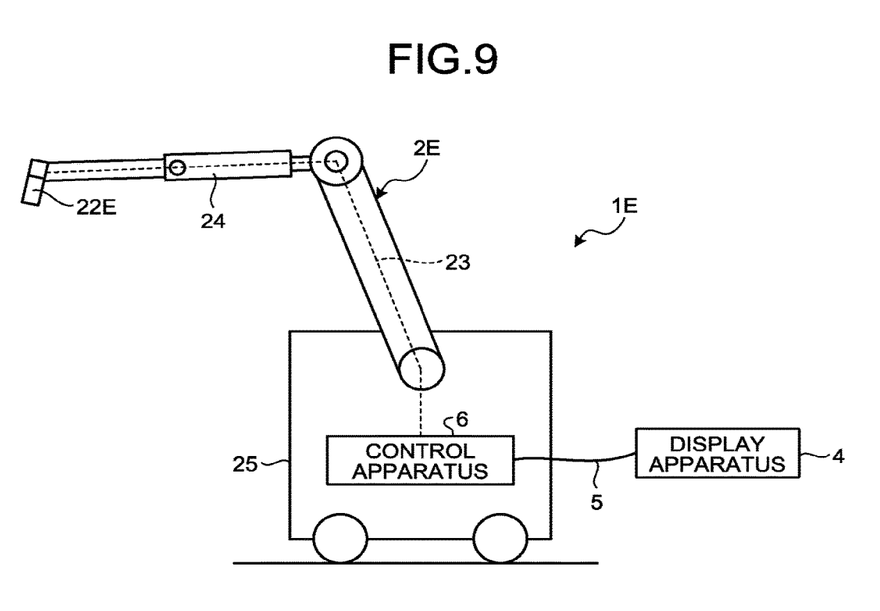
FIG. 9 is a diagram of a modification of the embodiment of the present disclosure, which is a diagram illustrating a schematic configuration of a medical observation system according to the present modification.

FIG. 9 is a diagram of a modification of an embodiment of the present disclosure, which is a diagram of a schematic configuration of a medical observation system 1E according to the modification.

Although the present disclosure is applied to the endoscope 2 including the camera head 22 in the medical observation system 1 according to the embodiment, this is not limiting; the present disclosure may be applied to an operating microscope that images a certain sight area of the inside of a subject (the inside of a living body) or the surface of a subject (the surface of a living body) in a magnified manner as in the medical observation system 1E illustrated in FIG. 9.

The medical observation system 1E according to the present modification includes an operating microscope 2E that takes an image for observing the subject to generated an image signal, the control apparatus 6 that processes the image signal generated by the operating microscope 2E, and the display apparatus 4 that is connected to the control apparatus 6 via the second transmission cable 5 to display an image for observation based on a video signal processed by the control apparatus 6.

As illustrated in FIG. 9, the operating microscope 2E includes a microscope unit 22E that images a minute site of the subject in a magnified manner to generate an image signal, a support unit 24 including an arm that is connected to the basal end of the microscope unit 22E to rotatably support the microscope unit 22E, and a base unit 25 that rotatably holds the basal end of the support unit 24 and may move on the surface of a floor.

The control apparatus 6 is installed in the base unit 25.

The base unit 25 may be fixed to a ceiling, a wall face, or the like to support the support unit 24, not movably provided on the surface of the floor.

The base unit 25 may include a light source unit that generates illumination light illuminating the subject from the operating microscope 2E.

The microscope unit 22E incorporates an imaging unit that images the subject to generate the image signal and a configuration similar to that of the programmable logic device 224 described in the embodiment, although their specific illustration is omitted, and processes the image signal generated by the imaging unit by the programmable logic device. The image signal processed by the microscope unit 22E (the programmable logic device) is transmitted to the control apparatus 6 via the first transmission cable 23 routed along the support unit 24.

Although the memory unit 2241C included in the communication functional block 2241 is initialized to reset only the communication functional block 2241 in the embodiment, this is not limiting.

The programmable logic device 224 may employ a configuration that partially performs configuration to reconstruct only the communication functional block 2241 (reset only the communication functional block 2241), for example. This holds true for the other programmable logic devices 611, 622, and 632.

Although the embodiment employs PCIe as the interface IF, another interface may be employed so long as it is an interface compliant with the communication interface standard (the PC/AT compatible standard, for example) and is communicable at a transmission rate of 1 Gbps or more.

Although the programmable logic devices 224, 611, 622, and 632 include the FPGA in the embodiment, this is not limiting; a complex programmable logic device (CPLD) or the like may be employed.

In the embodiment, at least part or the whole of the programmable logic device 224 provided in the camera head 22 may be provided on the first transmission cable 23 side such as the connector CN2. Similarly, at least part or the whole of the programmable logic device 611 provided in the control apparatus 6 (the interface module 61) may be provided on the first transmission cable 23 side such as the connector CN1.

The medical signal processing apparatus according to the present disclosure includes a programmable logic device having a plurality of functional blocks. The medical signal processing apparatus may individually reset a communication functional block among the functional blocks, not the entire programmable logic device. In other words, even when a communication error occurs (when an abnormality occurs in the communication functional block), only the communication functional block among the functional blocks is reset to restore a state in which an image signal may be communicated.

Consequently, the medical signal processing apparatus according to the present disclosure produces an effect of making it possible to restore a state in which the image signal may be communicated quickly even when a communication error occurs compared with a conventional configuration in which when an abnormality occurs in the functional block, the entire FPGA is reconstructed.

The medical observation system according to the present disclosure includes the medical signal processing apparatus and thereby produces an effect similar to that of the medical signal processing apparatus.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical signal processing apparatus for receiving input of an image signal corresponding to an inspection result of a subject and processing the image signal, the medical signal processing apparatus comprising:
a programmable logic device including a plurality of functional circuits, one functional circuit among the functional circuits being a communication functional circuit configured to communicate the image signal to another external device different from the medical signal processing apparatus, wherein
the communication functional circuit is individually resettable among the functional circuits such that the communication functional circuit is resettable without reconstructing the entire programmable logic device.

2. The medical signal processing apparatus according to claim 1, further comprising a memory that stores therein abnormality information indicating an abnormality in the communication functional circuit, wherein reset of the communication functional circuit is executed by initialization of the memory.

3. The medical signal processing apparatus according to claim 2, wherein the communication functional circuit includes the memory.

4. The medical signal processing apparatus according to claim 1, wherein
the communication functional circuit includes:
a signal processor that executes signal processing; and
an error detector circuit that detects an abnormality in the signal processor and outputs an error signal when detecting the abnormality, and
another functional circuit among the functional circuit is a reset functional circuit that resets only the communication functional circuit among the functional circuit in response to the error signal from the error detector circuit.

5. The medical signal processing apparatus according to claim 1, wherein another functional circuit among the functional circuit is a reset functional circuit that individually resets the communication functional circuit among the functional circuit in response to a reset signal output from the external device.

6. The medical signal processing apparatus according to claim 1, wherein power-on reset is executable that resets all of the functional circuits when the medical signal processing apparatus is powered on and the communication functional circuit is individually resettable among the functional circuits at a timing different from the power-on reset.

7. The medical signal processing apparatus according to claim 1, wherein the communication functional circuit is individually resettable among the functional circuits immediately after startup of the medical signal processing apparatus.

8. The medical signal processing apparatus according to claim 1, wherein the communication functional circuit is a high speed serial interface that communicates the image signal at a transmission rate of 1 Gbps or more to the external device.

9. The medical signal processing apparatus according to claim 1, wherein the communication functional circuit communicates a signal in which a clock is superimposed on the image signal to the external device.

10. A medical observation system comprising:
a medical signal processing apparatus configured to receive input of an image signal corresponding to an inspection result of a subject and process the image signal, the medical signal processing apparatus including:
a programmable logic device including a plurality of functional circuits, one functional circuit among the functional circuits being a communication functional circuit configured to communicate the image signal to another external device different from the medical signal processing apparatus, wherein the communication functional circuit is individually resettable among the functional circuits such that the communication functional circuit is resettable without reconstructing the entire programmable logic device; and
a display that displays an image for observation corresponding to the image signal processed by the medical signal processing apparatus,
wherein the communication functional circuit is individually resettable among the functional circuits only in a period until the display displays the image for observation after the medical signal processing apparatus is powered on.

* * * * *